United States Patent [19]

Wittmaack

[11] Patent Number: 4,982,090

[45] Date of Patent: Jan. 1, 1991

[54] METHOD AND APPARATUS FOR THE QUANTITATIVE, DEPTH DIFFERENTIAL ANALYSIS OF SOLID SAMPLES WITH THE USE OF TWO ION BEAMS

[75] Inventor: Klaus Wittmaack, Munich, Fed. Rep. of Germany

[73] Assignee: Gesellschaft für Strahlen- und Umweltforschung mbH (GSF), Neuherberg, Fed. Rep. of Germany

[21] Appl. No.: 305,693

[22] Filed: Feb. 2, 1989

[30] Foreign Application Priority Data

Feb. 5, 1988 [DE] Fed. Rep. of Germany ....... 3803424

[51] Int. Cl.$^5$ .......................................... H01J 37/252
[52] U.S. Cl. .................................. 250/309; 250/305; 250/306; 250/288
[58] Field of Search ............... 250/309, 305, 282, 288, 250/306

[56] References Cited

U.S. PATENT DOCUMENTS

| | | | |
|---|---|---|---|
| 3,415,985 | 12/1968 | Castaing et al. | 250/309 |
| 3,916,190 | 10/1975 | Valentine et al. | 250/309 |
| 4,088,895 | 5/1978 | Martin | 250/309 |
| 4,633,084 | 12/1986 | Gruen et al. | 250/309 |
| 4,670,651 | 6/1987 | Meier et al. | 250/309 |
| 4,860,224 | 8/1989 | Cashell et al. | 250/309 |

Primary Examiner—Jack I. Berman
Assistant Examiner—Kiet T. Nguyen
Attorney, Agent, or Firm—Spencer & Frank

[57] ABSTRACT

A method and an apparatus for the quantitative depth analysis of a solid sample by backscatter analyzing the sample with the light ions, removing a thin layer of the sample by sputter etching, using a beam of medium-mass or high-mass ions to bombard the sample, backscatter analyzing the sputter etched sample, and repeatedly performing the steps of removing a thin layer of the sample and backscatter analyzing the sputter etched sample. An apparatus for performing the method includes an analysis chamber for retaining the sample to be analyzed, and first and second accelerators. The first accelerator generates fast, light ions with an energy from about 0.1 MeV to about 5.0 MeV to be directed into the chamber onto a predetermined region of the sample at a first desired predetermined bombardment angle so that the fast ions are scattered by the ions of the sample. The second accelerator accelerates a beam of slow medium-mass or high-mass ions with an energy from about 0.5 to about 10.0 keV to be directed onto the predetermined region of the sample at a second desired predetermined bombardment angle. The analysis chamber has a sample manipulator for manipulating the sample and an analyzer for determining the energy of the fast ion scattered by the atoms of the sample.

13 Claims, 3 Drawing Sheets

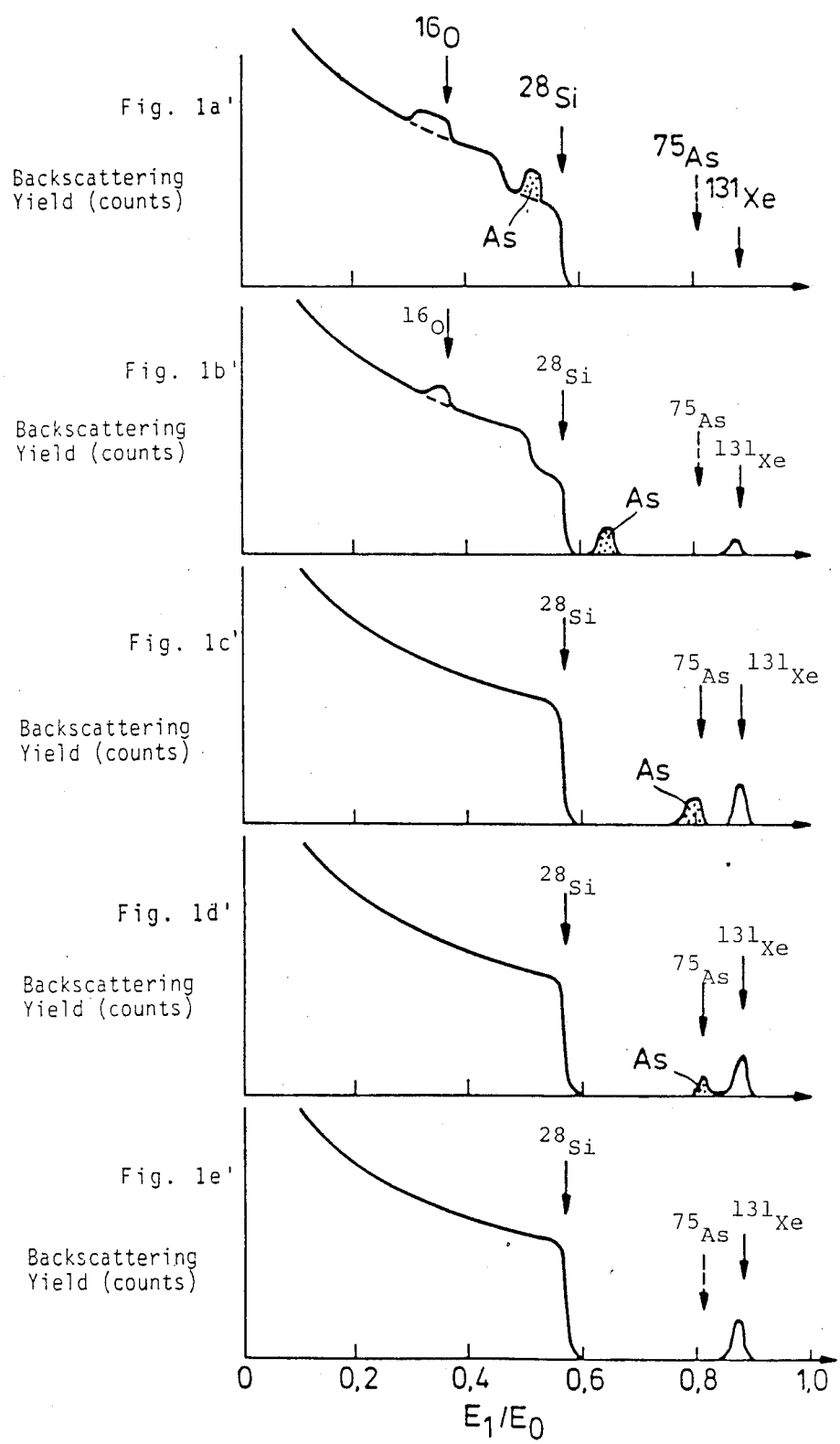

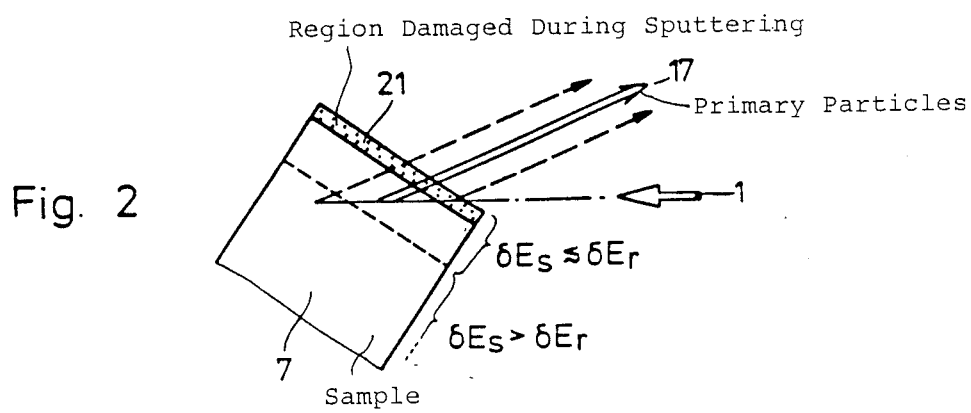
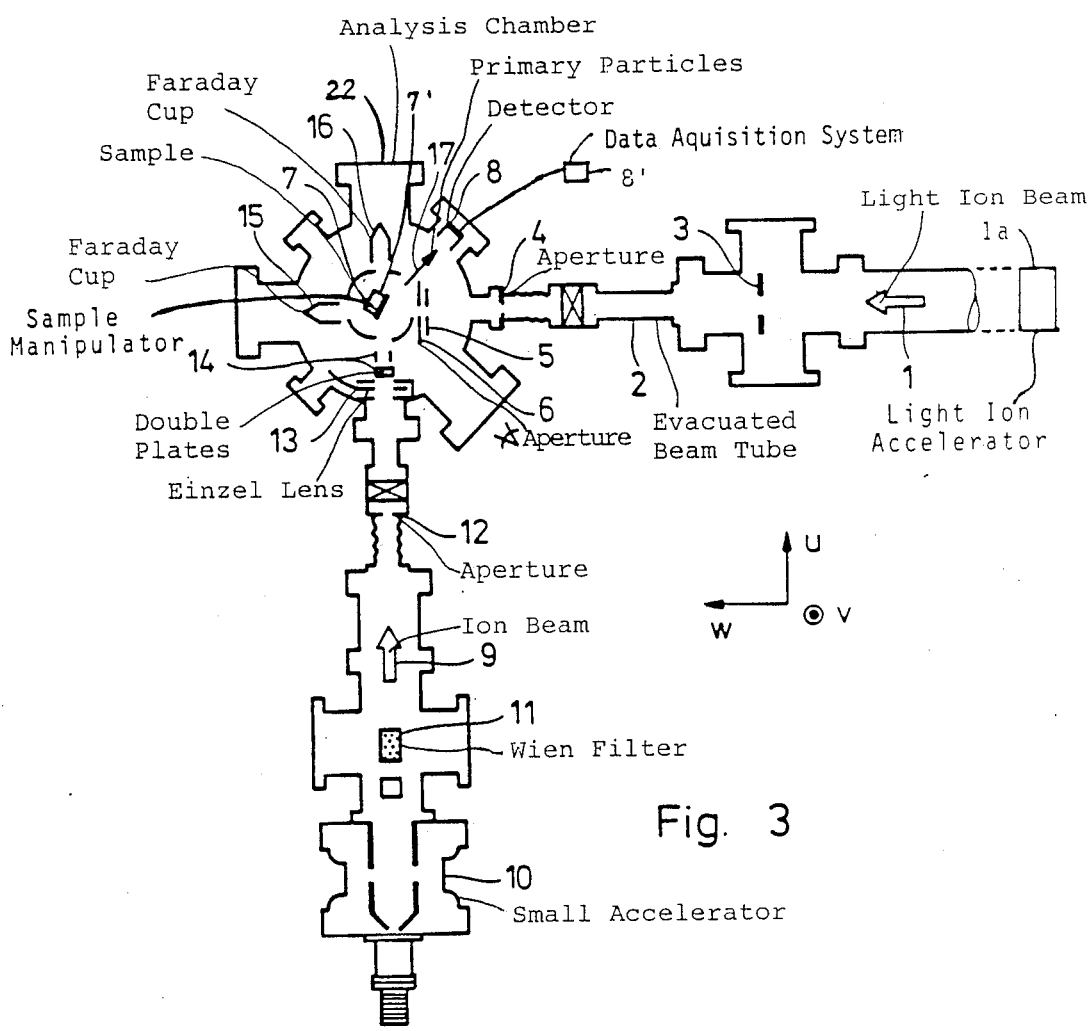

METHOD AND APPARATUS FOR THE QUANTITATIVE, DEPTH DIFFERENTIAL ANALYSIS OF SOLID SAMPLES WITH THE USE OF TWO ION BEAMS

BACKGROUND OF THE INVENTION

The invention relates to a method and apparatus for quantitative, depth differential analysis of solid samples with the use of two ion beams, namely by Rutherford backscattering of light ions and by sputter erosion due to bombardment with medium-mass or high-mass ions. The invention is based on the idea that the analytical potential of the Rutherford backscattering technique can be broadened and increased substantially if this method is employed in combination with sputter sectioning of the sample.

The principle and uses of backscattering spectrometry are described in detail in the book by Wei-Kan Chu, James W. Mayer and Marc-A. Nicolet, entitled *Backscattering Spectrometry*, published by Academic Press, New York, 1978. The nomenclature employed in this book will also be essentially employed in the description of the invention given below. References to relevant equations or paragraphs of the book will be preceded by "Chu et al".

The backscattering spectrometry method employs a beam of fast, light ions (i.e. $He^+$ or $He^{2+}$) which is directed onto a sample. The desired information about the composition of the sample is obtained by measuring the energy spectrum of the primary particles which are scattered into the solid angle $\Delta\Omega$ around angle $\theta$. If an atom of mass $M_2$ is located at a depth z of the sample, with z being measured perpendicularly to the surface of the sample, a primary particle of mass $M_1$ and an initial energy $E_0$, after being scattered off $M_2$, exhibits the energy $E_1$ when leaving the sample. This energy can be expressed as follows (Chu et al, §§3.2.1 and 3.2.2):

$$E_1 = KE_0 - [\epsilon]Nz \qquad (1)$$

with the stopping cross section factor $[\epsilon]$ being given by $$[\epsilon] = K\epsilon_{in}/\cos\theta_{in} = (\epsilon_{out}/\cos\theta_{out}) \qquad (2)$$

where K is the so-called kinematic factor which, for a given scattering angle $\theta$ (the angle between the directions of the incoming particle, and the exiting particle after scattering), depends only on the mass ratio $M_2/M_1$ (Chu et al, §2.2 as well as Tables II to V). The value $\bar{\epsilon}$ indicates the mean stopping cross section of the sample for the primary particle along its path between the surface and the scattering center. Subscripts 'in' and 'out' designate the incoming and exiting particle, respectively. The symbols $\theta_{in}$ and $\theta_{out}$ signify the angles between the surface normal and the propagation directions of the incoming and exiting particle bundle. N is the density of the sample in atoms/cm³ (See Chu et al. §§3.2.1 and 3.2.2).

Without other knowledge about the composition of the sample being examined, Equation (1) cannot be solved since it is—even with the knowledge of $\bar{\epsilon}$—an equation with two unknowns, namely K and z.

SUMMARY OF THE INVENTION

It is therefore an object of the present invention to modify the above-described method in such a way that the equivocality of the backscattering spectrum is eliminated.

According to the invention this problem is solved in steps. Initially a spectrum is recorded of the untreated sample (hereafter called the virgin spectrum). Then a beam of slow, heavy ions (e.g. $Ar^+$) is employed to remove a layer thickness element $\Delta z_j$ from the sample by sputtering, whereupon a further backscattering spectrum is recorded (spectrum j). Because of the removal of the layer of thickness $\Delta z_j$, the characteristic structures observed in the virgin spectrum are shifted in spectrum j, according to Equation (1), toward higher energies by the following amount:

$$\Delta E_{1,j} = [\bar{\epsilon}]N\Delta z_j \qquad (3)$$

By measuring $\Delta E_{1,j}$ and $\Delta z_j$ it is now possible, according to Equation (2) and with the knowledge of $\theta_{in}$ and $\theta_{out}$, to unequivocally determine K and thus $M_2$ if the energy dependent stopping cross section $\epsilon = \epsilon(E)$ is known from literature values (e.g. from Chu et al, Table VI, pages 362, 363). This situation exists if a sample having unknown impurities but known major components.

If $\epsilon(E)$ is unknown, then the removal of the sample material by sputtering must continue until the atoms of mass $M_2^*$, which produce a characteristic structure in the back-scattered spectrum, reach the instantaneous surface. In this case, the instantaneous depth z' defined by the following equation $$z' = z - \sum_{j=0}^{k} \Delta z_j \qquad (4)$$

has become zero so that $K(M_2^*)$ is unequivocally determined according to Equation (1), i.e.

$$K(M_2^*) = E_1(z'=0)/E_0 \qquad (5)$$

BRIEF DESCRIPTION OF THE DRAWINGS

FIGS. 1a'–1e' are graphs of the energy spectrum of the sample at the respective stages shown in FIGS. 1a–1e;

FIG. 2 is a schematic illustration of a backscattering analysis of a sputtered sample at a glancing angle of incidence; and FIG. 3 schematically illustrates a structural arrangement according to the invention.

DESCRIPTION OF THE PREFERRED EMBODIMENT

The invention will now be described in greater detail with reference to a simple example and FIGS. 1 to 3.

Figure 1A:
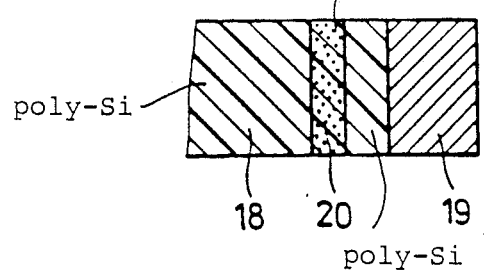
FIGS. 1a–1e are respective schematic cross-sectional views of a sample to be analyzed at five successive stages of sputtering.
Figure 1B:
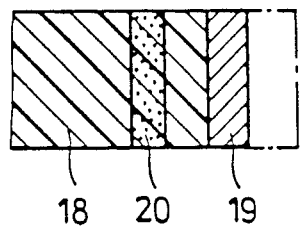
Figure 1C:
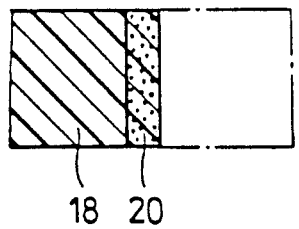
Figure 1D:
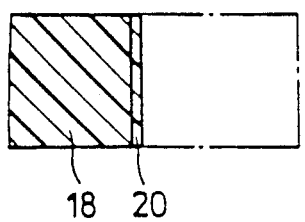
Figure 1E:
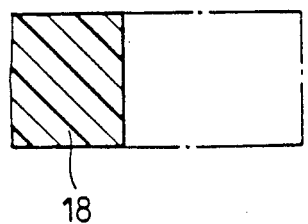

Let it be assumed that the sample is a multi-layer sample having the structure shown in FIG. 1a. A thick layer 18 of polycrystalline silicon (poly-Si) is deposited on a substrate, which is not of interest here, and is covered with a layer 19 of silicon dioxide ($SiO_2$). A narrow region 20 of the poly-Si layer 18 is doped with arsenic.

The backscattering spectrum of such a sample is shown schematically in FIG. 1a'. The vertical arrows identify, according to Equation (5), the relative energy $E_1(z'=0)/E_0$ for elements $^{16}O$, $^{28}Si$, $^{75}As$ and $^{131}Xe$. If now—as shown in FIGS. 1b to 1e—thin layers are sputtered away in stages, for example by bombarding the sample with xenon ions of an energy of a few keV, the backscattering spectra will change in the manner shown in FIGS. 1b' to 1e'. Using Equations (5) and (1), it is possible to identify, from the position of the characteristic stages and maxima and possibly their shift during continued sputtering, the elements contained in the sample and their position and depth in the sample.

The approach according to the invention is primarily of great utility if, as in the example of FIG. 1, impurity or doping elements of mass $M_{2,i}$ are present at a depth $z > z_{i,m}$ in a matrix of lighter atoms which have a mass $M_{2,m}$, where $$z_{i,m} = (K_i - K_m) E_0 / N[\bar{\varepsilon}] \qquad (6)$$

where $K_i$ and $K_m$ are, respectively, the kinematic factors for the impurity element of mass $M_{2,i}$ and the lighter atoms of mass $M_{2,m}$.

In this case, the signals generated by the two types of atoms (the impurity and the lighter atoms) are superposed in the backscattering spectrum at energy $E_1$ in FIG. 1a' the arsenic signal shows up on a "background" due to silicon in $SiO_2$). The "background", which is very annoying for a quantitative determination of the concentration of $M_{2,i}$ atoms, can be eliminated if a layer of a thickness $\Delta z$ is removed from the sample by sputtering so that $z - \Delta z < z_{i,m}$ (see migration of the arsenic signal in FIGS. 1a' to 1c').

A second advantage of the method according to the invention is that a combination of the backscattering method with bombardment induced sputtering permits the analysis also of deep lying regions in the sample. Without sputter sectioning, the maximum depth $z_{max}$ detectable during backscattering can be estimated with the aid of Equation (1) by setting the backscattering energy $E_1$ to zero, i.e.

$$z_{max} = KE_0 / N[\bar{\varepsilon}] \qquad (7)$$

The limitation defined by Equation (7) can be overcome according to the invention if, between two successive backscattering analyses, a layer of suitable thickness $\Delta z_j$ is removed from the sample. In order to determine the composition of the sample continuously as a function of the depth, the thickness $\Delta z_j$ should be selected in such a way that the backscatter spectra determined before and after atomization overlap in part, i.e.

$$\Delta z_j = \beta z_{max} \qquad (8)$$

with $$0.2 < \beta \leq 0.7$$

A third advantage of the method according to the invention relates to the possibility of performing backscattering analyses (see Chu et al, §§7.4, 7.5) with great depth resolution not only in the vicinity of the surface but also at a greater depth. According to Equation (1), the depth resolution $\delta z$ can be represented as follows $$|\delta z| = \delta E_1 / N[\bar{\varepsilon}] \qquad (9)$$

It follows from Equation (9) that $\delta z$ becomes smaller, i.e. the depth resolution becomes better, the smaller is $\delta E_1$ and the larger is $[\bar{\varepsilon}]$. The energy width $\delta E_1$ is composed of two parts, the given energy resolution $\delta E_r$ of the backscattering arrangement and the energy straggling $\delta E_s$ (Chu et al, §7.4) which, in the Gaussian approximation, is given by:

$$\delta E_1 = \{(\delta E_r)^2 + (\delta E_s)^2\}^{\frac{1}{2}} \qquad (10)$$

Energy straggling increases in proportion to the square root of the path length traversed by the beam in the sample. A good energy resolution $\delta E_r$ can thus be utilized fully only if $\delta E_s < \delta E_r$, i.e. the depth range that can be analyzed with a narrow energy width $\delta E_1$ is limited. This applies particularly if, for the purpose of high depth resolution $\delta z$, the backscattering measurement is performed at a glancing angle of incidence and/or exit of the analyzing beam so that $[\bar{\varepsilon}]$ becomes large (see Equations 2 and 9 as well as Chu et al, §7.5). The region covered with high depth resolution then becomes very narrow. According to the present invention one can analyze the sample with high depth resolution also at a greater depth if sample material is removed in steps by way of sputtering. In this case it is useful to perform the sputtering with heavy ions (e.g. $Xe^+$) of an energy of less than 1 keV and by bombarding at a glancing angle of incidence ($\theta_{sputtering} > 60°$). In this way the region 21, which was radiation damaged during sputtering, will extend only to a small depth from the instantaneous surface (see FIG. 2).

An arrangement for implementing the method according to the invention is shown in FIG. 3. The beam of fast, light ions 1 is produced by a conventional accelerator 1a with associated analysis magnet (not shown in detail here). On its path along the evacuated beam tube 2, the beam is collimated by means of apertures 3 to 6 before it impinges on a sample 7 (which is shown in detail in FIG. 1a) on a conventional sample manipulator 7' in analysis chamber 22 as schematically illustrated in FIG. 3. Sample 7 can be rotated about the v axis perpendicular to the plane of the drawing and can be moved in the directions of the u, v and w axes, by manipulator 7'. The primary particles 17 which are backscattered from atoms of sample 7 generate a signal in detector 8 which is processed in an electronic data acquisition system 8' schematically illustrated in FIG. 3.

The ion beam 9 used for the sputtering is generated by means of a small accelerator 10. In order to filter its velocity (or its mass, at a given beam energy) beam 9 passes through a Wien filter 11 and an aperture 12. Beam 9 is focused on sample 7 by means of an Einzel lens 13. By applying suitable, time-dependent voltages across a pair of double plates 14, the focused beam can be master scanned in a TV pattern over sample 7 so that an area of a magnitude $A_s$ is bombarded with a constant current density when averaged over time. This ensures uniform removal of material from sample 7 (having portions 18-20) over area $A_s$. To be able to realize a high removal rate with a given current of ion beam 9, area $A_s$ should be equal to or only slightly larger than the area $A_r$ covered by the analyzing beam 1.

For analyses of bombardment at a glancing angle of incidence, i.e. at $80° < \theta_{in} < 90°$, it is appropriate to give one or several of apertures 4 to 6 a slit shape so that the slit width $b_u$ is much less than the slit height $b_v$. With a sufficiently small divergence of beam 1, it is possible, in the case of $b_u = b_v \cos \theta_{in}$, to give $A_r$ a square shape with edges of a length $b_v$.

Absolute measurements of the ion currents incident on sample 7 can be performed by means of Faraday cups 15 and 16, respectively. For a current measurement, the sample must not intercept the respective beam. This can be accomplished by moving the sample in one of directions u, v and w.

No limitations exist with respect to the arrangement of the axes of beams 1 and 9 relative to one another. It must merely be ensured that sample 7 can be irradiated by both beams 1 and 9 at freely selectable bombardment angles.

The present disclosure relates to the subject matter disclosed in the Federal Republic of Germany, P No. 38 03 424.7 on Feb. 5th, 1988, the entire specification of which is incorporated herein by reference.

It will be understood that the above description of the present invention is susceptible to various modifications, changes and adaptations, and the same are intended to be comprehended within the meaning and range of equivalents of the appended claims.

What is claimed is:

1. A method for the quantitative depth differential analysis of a solid sample, comprising the steps of:
   (a) backscatter analyzing the sample with light ions;
   (b) removing a thin layer of the sample by sputter etching, using a beam of medium-mass or high-mass ions to bombard the sample;
   (c) backscatter analyzing the sputter etched sample; and
   (d) repeatedly performing said steps (b) and (c).

2. A method as in claim 1, wherein each backscatter analyzing step includes a step of directing said light ions onto the sample at a glancing incidence and each said step of removing includes the step of directing the beam of medium-mass or high-mass ions onto the sample at low ion energy and so as to have a glancing incidence on the sample, whereby both shallow and deep lying regions of the sample are exposable for analysis with high depth resolution.

3. A method as in claim 1, wherein each backscatter analyzing step includes a step of detecting the backscattered light ions at a glancing angle of emergence, and each step of removing by sputter etching includes the step of directing the beam of medium-mass or high-mass ions onto the sample at a low ion energy and so as to have a glancing incidence on the sample, whereby both shallow and deep lying regions of the sample are exposable for analysis with high depth resolution.

4. A method as in claim 10, wherein each backscatter analyzing step includes a step of directing said light ions onto the sample at a glancing incidence.

5. A method as in claim 1, wherein each backscatter analyzing step includes a step of directing said light ions onto the sample at a glancing incidence.

6. An apparatus for the quantitative depth differential analysis of a solid sample, comprising:
   analysis chamber for holding therein the sample to be analyzed;
   first accelerator means for generation a beam of fast, light ions with an energy in a range from about 0.1 MeV to about 5 MeV and directing the beam of fast ions into said chamber onto a predetermined region of the sample at a desired bombardment angle so that the fast ions are scattered by the atoms of the sample in the predetermined region thereof; and
   second accelerator means for generating a beam of slow, medium-mass or high-mass ions with an energy of about 0.5 to about 10 keV and directing the beam of slow ions onto the predetermined region of the sample at a second desired predetermined bombardment angle, said analysis chamber having a sample manipulator means for manipulating the sample and means for determining the energy of the fast ions scattered by the atoms of the sample.

7. An apparatus as in claim 6, wherein the fast ions are selected from the group of ions consisting of $H^+$, $He^+$, $He^{2+}$ and $Li^+$.

8. An apparatus as in claim 7, wherein the slow ions are inert gas.

9. An apparatus as in claim 7, wherein the slow ions comprise $Ar^+$.

10. An apparatus as in claim 7, wherein the slow ions comprise $Xe^+$.

11. An apparatus as in claim 6, wherein the slow ions are inert gas.

12. An apparatus as in claim 6, wherein the slow ions comprise $Ar^+$.

13. An apparatus as in claim 6, wherein the slow ions comprise $Xe^+$.

* * * * *